United States Patent [19]

Evans et al.

[11] Patent Number: 4,731,469

[45] Date of Patent: Mar. 15, 1988

[54] PROCESS FOR RECOVERY AND PURIFICATION OF L-PHENYLALANINE

[75] Inventors: David L. Evans, Arvada; Roberta L. Thimmig, Brighton; Robert C. Koltz, Lafayette, all of Colo.

[73] Assignee: Synthetech, Inc., Boulder, Colo.

[21] Appl. No.: 894,239

[22] Filed: Aug. 6, 1986

[51] Int. Cl.$^4$ .............................................. C07C 99/12
[52] U.S. Cl. .................................................. 562/443
[58] Field of Search ........................................ 562/443

[56] References Cited

U.S. PATENT DOCUMENTS

| | | | |
|---|---|---|---|
| 2,880,179 | 3/1959 | Comar | 562/443 |
| 4,384,136 | 5/1983 | Steinmetzer | 562/444 |
| 4,536,596 | 8/1985 | Savides et al. | 562/443 |
| 4,574,117 | 3/1986 | Vollmer et al. | 435/108 |
| 4,584,269 | 4/1986 | Vollmer et al. | 435/108 |
| 4,584,273 | 4/1986 | Finkelman et al. | 435/108 |
| 4,584,399 | 4/1986 | Portal et al. | 562/443 |
| 4,584,400 | 4/1986 | Otani et al. | 562/443 |
| 4,604,483 | 8/1986 | Kitsukawa et al. | 562/443 |

FOREIGN PATENT DOCUMENTS

| | | | |
|---|---|---|---|
| 0140713 | 8/1985 | European Pat. Off. | 562/443 |
| 59-39857 | 3/1984 | Japan | 562/443 |
| 1489468 | 10/1977 | United Kingdom | 562/443 |

OTHER PUBLICATIONS

Yamada et al., "Production of L-Phenylalanine from trans-Cinnamic Acid with *Rhodotorula glutinis* Containing L-Phenylalanine Ammonia-Lyase Activity," Applied Environmental Microbiology, vol. 42, pp. 773-778, Aug. 1981.

Calton et al., "The Production of L-Phenylalanine by Polyazetidine Immobolized Microbes," Bio/Technology, vol. 4, (Apr. 1986).

*Primary Examiner*—James H. Reamer
*Attorney, Agent, or Firm*—Sheridan, Ross & McIntosh

[57] ABSTRACT

This invention concerns a process for the recovery and purification of L-phenylalanine from a reaction mixture containing L-phenylalanine and contaminants.

18 Claims, No Drawings

PROCESS FOR RECOVERY AND PURIFICATION OF L-PHENYLALANINE

FIELD OF THE INVENTION

This invention relates to the recovery and purification of L-phenylalanine from a reaction mixture containing L-phenylalanine and contaminants. Contaminants can include L-phenylalanine precursors, L-phenylalanine production by-products, and other compounds.

BACKGROUND OF THE INVENTION

There are several methods reported for producing L-phenylalanine. In one such method, L-phenylalanine is produced by contacting trans-cinnamic acid and ammonium ions in the presence of the enzyme L-phenylalanine ammonia-lyase (PAL) produced by strains of microorganisms. This procedure is known and described in U.S. Pat. No. 4,584,269, which is directed toward a method for producing L-phenylalanine and preserving the useful life of the enzyme by conducting the reaction under substantially anaerobic conditions. U.S. Pat. No. 4,584,273 describes a process for the production of L-phenylalanine ammonia-lyase by fermentation. The stability and useful life of the enzyme is improved by maintaining the enzyme in anaerobic, static conditions. U.S. Pat. No. 4,574,117 discloses a method for producing L-phenylalanine using PAL. Reducing agents are added to the process to minimize the effects of oxygen on the enzyme.

Yamada, et al., Production of L-Phenylalanine From Trans-Cinnamic Acid With *Rhodotorula glutinis* Containing L-Phenylalanine Ammonia-lyase Activity, Applied Environmental Microbiology, Vol. 42. p. 773, Aug. 1981, describe the use of *Rhodotorula glutinis* for the enzymatic conversion of trans-cinnamic acid to L-phenylalanine.

U.K. Pat. No. 1,489,468 (1977) teaches the use of the enzyme to convert trans-cinnamic acid and ammonium ions to L-phenylalanine by adjusting the concentration of the reactants to drive the reaction towards L-phenylalanine production instead of its breakdown.

L-phenylalanine can also be produced by transaminating phenylpyruvate. Calton, et al., in "The Production of L-Phenylalanine By Polyazetidine Immobilized Microbes", Bio/Technology, Vol. 4 (April 1986) describe the production of L-phenylalanine by the transamination of phenylpyruvate using aspartic acid. The ragents are contacted in the presence of a microorganism capable of producing sufficient amounts of the transaminase used to enzymatically catalyze the transamination. Pyruvic acid, or its salts, is a by-product of this method and constitutes a contaminant that must be separated from L-phenylalanine.

Recovery of L-phenylalanine was discussed in Yamada, et al. Yamada describes the use of ion exchange techniques for the separation of L-phenylalanine from a reaction mixture containing L-phenylalanine and L-phenylalanine precursors.

U.K. Pat. No. 1,489,468 (1977) describes the separation of L-phenylalanine from a reaction mixture by use of ion exchange techniques followed by recrystallization. The reference also discloses that L-phenylalanine can be alternately isolated by filtration and azeotropic distillation with benzene.

U.S. Pat. No. 4,584,399 discloses a method for separating L-phenylalanine from an aqueous solution by contacting the solution with activated carbon and then eluting L-phenylalanine from the activated carbon followed by ion exchange to remove further contaminants and then crystallization of L-phenylalanine.

U.S. Pat. No. 4,584,400 describes a process for separating L-phenylalanine and tyrosine by using a nonpolar, porous synthetic adsorbant having a higher affinity for L-phenylalanine than tyrosine, followed by elution of L-phenylalanine from the adsorbant.

E.P. Pat. No. 0140713 (1985) discloses a procedure for the separation of L-phenylalanine by evaporation of a reactant mixture containing L-phenylalanine and L-phenylalanine precursors at reduced pressure and temperature until L-phenylalanine precipitates.

There are disadvantages to all of these separation processes. Separation of L-phenylalanine from a reaction mixture through the use of ion exchange columns or adsorbtion procedures has the disadvantage of being expensive due to the cost of the resins and/or adsorbants. In addition, after elution, one is left with a large volume of dilute solution which is difficult to handle and requires evaporation before further separation and purification can take place.

The process described in E.P. Pat. No. 0140713 is undesirable because it yields L-phenylalanine contaminated with unacceptable amounts of precursors such as trans-cinnamic acid.

Accordingly, there is the need for a purification process which can readily provide L-phenylalanine in substantially pure from and particularly minimize contamination with trans-cinnamic acid or pyruvic acid.

SUMMARY OF THE INVENTION

This invention involves a process for the recovery and purification of L-phenylalanine. The process comprises contacting a mixture containing L-phenylalanine and at least one contaminant with a lower alkyl alcohol at a temperature chosen to increase the solubility of the contaminant and dissolve substantially all of the contaminant and provide at least about 70 percent of the L-phenylalanine in solid form. In particular this invention involves a process for the recovery of L-phenylalanine from a mixture in which trans-cinnamic acid is a contaminant.

DETAILED DESCRIPTION OF THE PREFERRED EMBODIMENTS

The instant invention involves a process for recovering substantially pure L-phenylalanine from an aqueous mixture or slurry containing L-phenylalanine and contaminating materials. Normally this mixture contains L-phenylalanine, L-phenylalanine precursors such as trans-cinnamic acid, or by-products of L-phenylalanine production such as pyruvic acid. As used herein, trans-cinnamic acid or pyruvic acid are intended to include the cinnamate and pyruvate anions and/or their salts with cations such as ammonium ions in the system depending on the pH. The mixture can also contain L-phenylalanine contaminants for example buffer compounds such as ammonium sulfate, ammonium phosphate, ammonium formate, ammonium acetate, ammonium bicarbonate, ammonium carbonate, and ammonium carbamate, as well as organic and biological contaminants and colorants. In the instant process, a majority of the water is evaporated from the aqueous mixture or slurry forming a condensed mixture. A lower alkyl alcohol is then added to the condensed mixture to solubilize the precursors, by-products and other contaminants and allow recovery of the L-phenylalanine as a solid. This method of recovery is substantially different from the processes known in the art in which the precursor, such as trans-cinnamic acid, is removed as a solid while the L-phenylalanine remains in solution.

Surprisingly, it has now been found that the presence of a lower alkyl alcohol affects the solubilities of L-phenylalanine and certain contaminants such as trans-cinnamic acid in an aqueous mixture to allow recovery of L-phenylalanine in high purity as a solid. Thus, in a preferred temperature range which can be readily determined as discussed hereinbelow, the L-phenylalanine is substantially insoluble while the contaminants, precursors, by-products and other materials remain in solution. This provides L-phenylalanine as a substantially pure solid.

The instant process has advantages in addition to providing a substantially pure L-phenylalanine product. First, the phenylalanine product is in the form of an alcohol wet cake which is readily available for esterification, particularly with the alcohol used for the purification process. Second, the instant process allows a higher production rate or throughput of reactants for a given reactor volume. Since the instant recovery process is capable of recovering L-phenyulalanine in high purity even in the presence of substantial amounts of precursor or by-product, the L-phenylalanine reaction need not be carried out to high conversions as in the prior art. This allows the use of a shorter reaction time, i.e. shorter reactor residence time, which provides a higher throughput.

In the practice of the instant invention, L-phenylalanine is separated from a mixture by adding a lower alkyl alcohol or a mixture of lower alkyl alcohols to the mixture. As used herein the term "lower alkyl alcohol" means a $C_1$–$C_6$, straight-chain, branched-chain, or cyclic alcohol. Such alcohols include methanol, ethanol, n-propanol, isopropanol, n-butanol, 2-butanol, t-butanol, and cyclohexanol. The preferred alcohols are methanol, ethanol and isopropanol.

The lower alkyl alcohol can be added directly to the mixture from which L-phenylalanine is to be separated. However, when the mixture contains a substantial amount of water, it is preferred that the mixture or slurry be concentrated prior to the addition of the alcohol by removing a portion of the water to allow the handling of smaller volumes of mixture. This also normally allows less alcohol to be used. As used herein the term "mixture" is intended to include aqueous solutions and slurries containing L-phenylalanine and at least one other material which can contaminate the L-phenylalanine.

Concentration of the mixture to form a residue or sludge is preferably carried out under vacuum so that evaporation of water occurs at lower temperatures. When the desired product is L-phenylalanine and not a racemic mixture, it is important to minimize racemization during the purification process. Since racemization is time and temperature dependent, the longer the temperature remains elevated, the more racemization of L-phenylalanine will occur. Significant racemization of L-phenylalanine can occur at or above about 70° C. Therefore, it is preferred that removal of water take place at a bulk temperature below about 70° C. Preferably the L-phenylalanine should not be exposed to a temperature of above about 70° C. for more than 10 minutes. Other things being equal, the temperature at which water can readily be removed from the mixture can be decreased by imposing a vacuum on the system. The proper balance of temperature, system pressure and time can be readily determined by a person skilled in the art.

As water is removed from the mixture, the viscosity of the residue or sludge increases. Essentially all of the water can be removed from the sludge. The more water that is removed, the higher the recovery of L-phenylalanine. Therefore, to maximize L-phenylalanine recovery, the maximum amount of water is removed. However, decreasing the amount of water in the sludge below about 50 weight percent necessitates the use of special equipment to handle the viscous residue. If appropriate equipment is available or its use is desired, substantially all of the water can be removed from the mixture. Normally, it is preferred that the sludge contain at most about 50 weight percent water.

In the event that buffer compounds are present in the mixture which are either non-volatile or are not soluble in the water/lower alkyl alcohol solution, these materials can contaminate the solid L-phenylalanine which is recovered. Therefore, it is preferable that these materials be removed from the mixture prior to the addition of alcohol. Techniques such as the use of ion-exchange resins can be used to remove these materials. It is also possible to replace non-volatile buffer components with a volatile component through ion-exchange and subsequently remove the volatile material during evaporation of the water.

The resulting sludge, having about 50/50 weight ratio of water to solids, contains L-phenylalanine and the contaminants. According to the process of this invention, this sludge is then mixed with the lower alkyl alcohol. Sufficient alcohol is added to the sludge to insure that the contaminating materials will remain in solution at the temperature to which the mixture of sludge and alcohol is to be cooled. As used herein, the term "final temperature" is the temperature to which the mixture of sludge and alcohol is to be cooled. The preferred amount of alcohol is the minimum amount which when added to the sludge will dissolve substantially all contaminants and a minimum amount of the L-phenylalanine at the final temperature.

If desired, sufficient alcohol can be added to the sludge and the temperature of the mixture can be increased to dissolve substantially all of the solids present including the L-phenylalanine. The temperature of the solution can then be reduced to form solid L-phenylalanine. However, this procedure is ordinarily more time consuming than the procedure in which substantially all of the contaminants are dissolved while minimizing dissolution of L-phenylalanine. The complete dissolution method can be the method of choice if the mixture contains an insoluble contaminant such as the buffer discussed hereinabove. In that event, the insoluble contaminant can be removed by usual methods such as filtration followed by solidification of the L-phenylalanine.

A convenient method to determine the appropriate amount of alcohol to be added is the generation of solubility curves for the primary contaminant or contaminants with the desired alcohol. The solubility curves are generated by determining the solubility of the contaminant at different temperatures and different water/alcohol ratios. For example, if trans-cinnamic acid is the contaminant, solubility curves can be generated for trans-cinnamic acid by saturating solutions of varying water/alcohol ratios with trans-cinnamic acid at a particular temperature. For convenience, ambient temperature is ordinarily used. Each solution is then cooled to a given temperature with the temperature being maintained until the solution has equilibrated. At equilibrium, the solubility of trans-cinnamic acid is quantitatively determined by methods well known in the art, for example, High Performance Liquid Chromatography (HPLC). The solubility data of trans-cinnamic acid in each water/alcohol solution at a given temperature is used to generate a family of solubility curves.

For convenience, the family of solubility curves generated by plotting the solubility data can be mathematically fit to an appropriate equation by means known to those skilled in the art, for example, by using regression analysis.

The equation is used to detemine how much alcohol needs to be added to solubilize the trans-cinnamic acid at the final temperature.

Since the solubilities of the L-phenylalanine and contaminants are dependent upon temperature, the final temperature of the sludge, water/alcohol mixture is important. Preferably the temperature of the sludge and water/alcohol mixture is such that all of the contaminants are dissolved at the final temperature.

Once the alcohol is added, the sludge and water/alcohol mixture is cooled to provide for precipitation of L-phenylalanine and substantially none of the contaminants. Lower temperatures normally require larger amounts of alcohol to dissolve contaminants such as trans-cinnamic acid resulting in the dissolution of larger amounts of L-phenylalanine. Therefore, depending on the water/alcohol ratio and the alcohol used, there is an optimum temperature range for recovery of the L-phenylalanine. Usually the desired final temperature is determined first. The optimum temperature is usually one that encompasses all variables and parameters of the entire production process including, for example, available equipment for handling mixtures. When methanol is the alcohol and trans-cinnamic acid is the primary contaminant, it has been found that the preferred temperature range is between about 10° C. to about −20° C., most preferably about 0° C. to about −10° C. When the composition of the sludge is known, the amount of alcohol to be added can then be calculated.

After cooling, solid L-phenylalanine is separated from the alcohol phase by any standard means, such as filtration or centrifugation. The solid is then washed with fresh, cold alcohol to remove remaining contaminants. The wash alcohol is preferably as cold as possible down to the freezing point of the alcohol to provide for minimum dissolution of product in the wash solution. However, in normal commercial operations the cooling systems usually only provide for economical cooling down to approximately −20° C. If alternate cooling systems are available or desired, the wash solution can be cooled to a point limited only by the freezing point of the wash alcohol.

The resulting solid is an L-phenylalanine wet cake that can be used in other reaction processes, for example reactions where water is detrimental. If the desired final product is an L-phenylalanine ester, the alcohol of choice in the separation procedure just described is preferably the ester alcohol, for example, methanol is preferably used if L-phenylalanine methyl ester is the desired final product.

As discussed hereinabove, L-phenylalanine is conveniently produced by contacting trans-cinnamic acid and ammonium ions in the presence of an L-phenylalanine ammonia-lyase. The reaction is carried out in aqueous solution containing trans-cinnamic acid, ammonium ions, ammonia, buffer compounds, preferably ammonium bicarbonate, and L-phenylalanine ammonia-lyase. The enzyme can be provided by the addition of microorganisms capable of producing the enzyme or by adding the enzyme extracted from said microorganisms. The resulting reaction mixture from which L-phenylalanine is recovered can contain in addition to water, L-phenylalanine, unreacted trans-cinnamic acid, ammonium ions, buffer compounds, and organic and biological contaminants and colorants.

In a preferred embodiment of the instant invention, methanol is added to a sludge containing approximately 50 weight percent water as well as L-phenylalanine, trans-cinnamic acid and other contaminants to effect separation of L-phenylalanine from trans-cinnamic acid and other contaminants. About 2.24 grams of methanol is added per gram of sludge and the resulting mixture is cooled to about −10° C. At −10° C., substantially all of the trans-cinnamic acid and other contaminants are dissolved in the water/methanol but only about 20 percent to about 30 percent of the L-phenylalanine is dissolved.

The solid L-phenylalanine is then separated from the liquid layer by any standard separation procedure, such as filtration. The solid L-phenylalanine is then washed with cold methanol, ordinarily at least about −20° C. The resulting product is an L-phenylalanine methanol wet cake.

As previously stated, the method for recovering L-phenylalanine described in the instant process provides for recovery of about 70 percent of the L-phenylalanine contained in the sludge. The approximately 30 percent L-phenylanine not recovered as described above is not lost because substantially all of the compounds not consumed in the production of L-phenylalanine as well as the unrecovered L-phenylalanine are recycled. Trans-cinnamic acid, ammonium ions and ammonia are recovered for use in the production of L-phenylalanine. The alcohol used in the separation and purification of L-phenylalanine is recovered and recycled and any L-phenylalanine not recovered in the separation and purification steps is recycled into the system for the production of L-phenylalanine.

The instant process can also be used to recover substantially pure L-phenylalanine from reaction mixtures provided by other methods of L-phenylalanine production. For example, when L-phenylalanine is produced by the transmination of phenylpyruvate, the alcohol procedure described hereinabove is effective in recovering solid L-phenylalanine from the reaction mixture containing contaminants such as pyruvic acid, buffer compounds, and organic and biological compounds. Pyruvic acid is very soluble in cold lower alkyl alcohols used in the instant process whereas L-phenylalanine is not. Therefore, pyruvic acid and other contaminants will dissolve in the cold alcohol and L-phenylalanine can be recovered as a substantially pure solid.

The following examples are intended by way of illustration and not by way of limitation.

EXPERIMENTAL

EXAMPLE 1

Use of Methanol for Separation of L-phenylalanine from a Reaction Mixture

L-phenylalanine was produced by reacting trans-cinnamic acid and ammonium ions in the presence of an L-phenylalanine ammonia-lyase in a bioreactor column to approximately 70 percent conversion. The resulting mixture contained L-phenylalanine, trans-cinnamic acid, buffer compounds, organic and biological compounds in addition to colorants. The mixture was evaporated to approximately a 20 percent solids sludge containing 290 g L-phenylalanine, 119 g trans-cinnamic acid and 1.73 kg of water. Evaporation was carried out at a temperature of 60° C. at a pressure of approximately 3 psia (pounds per square inch absolute). 1.73 liters (l) of 25° C. methanol were added to the sludge to dissolve substantially all of the trans-cinnamic acid and compounds other than L-phenylalanine. This mixture was cooled to −10° C. with stirring, the solids were filtered from the methanol mixture and washed with 1.5 l of −20° C. methanol. The resulting methanol wet cake contained approximately 174 g of L-phenylalanine and 0.14 g of trans-cinnamic acid.

Calculation of Amount of Methanol to be Added to a Sludge

Solutions of varying water/methanol weight percents were saturated with trans-cinnamic acid at ambient temperature. The solutions were cooled to −20° C., −10° C. and 0° C. respectively and each system was allowed to come to equilibrium. At equilibrium, the solubility of trans-cinnamic acid was determined by HPLC. Solubility of trans-cinnamic acid in each solution system was determined at −20° C., −10° C., and 0° C. The solubility data was plotted to show the number of grams of trans-cinnamic acid soluble in varying water/methanol systems at a given temperature. A separate curve was generated for solubilities at each temperature. The solubility values were fit to an equation using regression analysis. The resulting equation was $$4.9 \times 10^{-6} T^2 x^2 + 5.95 \times 10^{-6} T^2 x + 2.96 \times 10^{-6} T^2 -$$
$$2.762 \times 10^{-4} Tx^2 + 7.477 \times 10^{-4} Tx + .000113 T +$$
$$.054454 x^2 - .007579 x + .00516 =$$

grams of trans-cinnamic acid per gram of solvent

T = Temperatue in °C.
Solvent = water plus methanol
x = weight fraction of methanol in solvent

EXAMPLE 2

L-phenylalanine was produced as described above. The mixture was evaporated to approximately 53 percent solids sludge. A 10 g sample of the sludge containing 3.60 g L-phenylalanine, 1.78 g trans-cinnamic acid was mixed with 41 ml of methanol and cooled to −20° C. The solids were filtered. 85 percent of the L-phenylalanine was recovered. The trans-cinnamic acid present as a contaminant was less than 0.08 percent.

EXAMPLE 3

A 50 ml solution containing 100 millimolar (mM) phenylalanine and 100 mM pyruvic acid was prepared and adjusted to a pH of 7.0 with 28 weight percent as (NH₃) ammonium hydroxide. The solution was evaporated under vacuum until a sludge of 66% water by weight was obtained. 10 ml of methanol were added to the sludge and the resulting mixture was cooled to a temperature of −20° C. The solids were filtered and washed with 10 ml of −20° C. methanol. The solids were weighed and analyzed for purity using High Performance Liquid Chromatography. The solids contained 0.1% pyruvic acid and corresponded to a phenylalanine recovery of 64%.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A process for the recovery and purification of L-phenylalanine from an aqueous mixture containing L-phenylalanine and at least one contaminant said process comprising evaporating water to provide a sludge having a solid phase and a liquid phase, adding sufficient lower alkyl alcohol to dissolve substantially all of the contaminant cooling said sludge to a final temperature to increase formation of solid L-phenylalanine at a pH of at least 7.0, and separating said solid L-phenylalanine from said liquid phase 2. The process of claim 1 wherein the lower alkyl alcohol is selected from the group consisting of methanol, ethanol, n-propanol, isopropanol, n-butanol, 2-butanol, t-butanol and cyclohexanol.

3. The process of claim 2 wherein said alcohol is methanol, ethanol or isopropanol.

4. The process of claim 1 wherein the final temperature is between about 10° C. and about −20° C.

5. The process of claim 3 wherein said alcohol is methanol and said final temperature is between about 10° C. and about −20° C.

6. The process of claim 1 wherein said contaminant comprises trans-cinnamic acid.

7. The process of claim 1 wherein said contaminant comprises pyruvic acid.

8. The process of claim 1 wherein said mixture is an aqueous mixture comprising L-phenylalanine, trans-cinnamic acid, and ammonium ions said process comprising:
 (a) forming the sludge comprising L-phenylalanine, trans-cinnamic acid and water;
 (b) adding an amount of said alcohol to said sludge to dissolve substantially all of said trans-cinnamic acid and form a slurry;
 (c) cooling said slurry to said final temperature to provide solid L-phenylalanine while maintaining substantially all of said trans-cinnamic acid in said liquid phase; and
 (d) separating said solid L-phenylalanine from said liquid phase.

9. The process of claim 8 wherein said alcohol is methanol.

10. The process of claim 9 wherein said final temperature is between about 10° C. and −20° C. to provide said solid L-phenylalanine.

11. The process of claim 1 wherein said liquid phase from which said solid L-phenylalanine has been separated is recycled to a reactor for the production of L-phenylalanine.

12. The process of claim 1 wherein sufficient water is evaporated to provide a sludge having at least about 50 weight percent solids.

13. A process for the recovery and purification of L-phenylalanine from an aqueous mixture comprising L-phenylalanine, ammonium ions and an L-phenylalanine precursor said process comprising:
  (a) evaporating sufficient water to provide a sludge having a solid phase and a liquid phase;
  (b) adding an amount of a lower alkyl alcohol to said sludge to dissolve substantially all of said L-phenylalanine precursor and form a slurry;
  (c) cooling said slurry to a final temperature to provide solid L-phenylalanine while maintaining substantially all of said precursor in said liquid phase;
  (d) maintaining a pH of said slurry of at least 7.0; and
  (e) separating solid L-phenylalanine from said liquid phase.

14. The process of claim 13 wherein sufficient water is evaporated in Step (a) to provide a sludge having at least about 50 weight percent solids and said final temperature in Step (c) is below about 10° C.

15. The method of claim 14 wherein said precursor is trans-cinnamic acid or pyruvic acid.

16. The method of claim 15 wherein said precursor is trans-cinnamic acid which is recycled to a reactor for the production of L-phenylalanine after separation from solid L-phenylalanine in Step (e).

17. The method of claim 16 wherein said alcohol is methanol.

18. The method of claim 1 wherein the amount of said alcohol is at least about 472 weight percent of said L-phenylalanine present in said mixture.

* * * * *

UNITED STATES PATENT AND TRADEMARK OFFICE
CERTIFICATE OF CORRECTION

PATENT NO. : 4,731,469

DATED : March 15, 1988

INVENTOR(S) : Evans et al.

It is certified that error appears in the above—identified patent and that said Letters Patent is hereby corrected as shown below:

Column 1, line 50, please delete the word "ragents" and insert -- reagents -- therefor.

Column 2, line 12, please delete the word "reactant" and insert -- reaction -- therefor.

Column 2, line 20, please insert before the word "ants" -- and the cost to regenerate the resins and/or absorbants --.

Column 6, line 56, please delete the word "transmination" and insert -- transamination -- therefor.

Column 7, line 9, please delete the word "hioreactor" and insert -- bioreactor -- therefor.

Signed and Sealed this

Eighteenth Day of October, 1988

Attest:

DONALD J. QUIGG

*Attesting Officer*  *Commissioner of Patents and Trademarks*